US00PP29394P2

(12) United States Plant Patent
Horvath

(10) Patent No.: US PP29,394 P2
(45) Date of Patent: Jun. 12, 2018

(54) ***AGASTACHE* HYBRID PLANT NAMED 'VELVET CRUSH'**

(50) Latin Name: ***Agastache* hybrid**
Varietal Denomination: Velvet Crush

(71) Applicant: Brent Arpad Horvath, Fontana, WI (US)

(72) Inventor: Brent Arpad Horvath, Fontana, WI (US)

( * ) Notice: Subject to any disclaimer, the term of this patent is extended or adjusted under 35 U.S.C. 154(b) by 0 days. days.

(21) Appl. No.: 15/530,327

(22) Filed: Dec. 27, 2016

(51) Int. Cl.
*A01H 5/02* (2018.01)

(52) U.S. Cl.
USPC ..... Plt./399
CPC ..... *A01H 5/02* (2013.01)

(58) Field of Classification Search
USPC ..... Plt./399
CPC ..... A01H 5/02
See application file for complete search history.

*Primary Examiner* — Kent L Bell

(57) ABSTRACT

A new, distinct *Agastache* hybrid plant as shown and described, characterized by the combination of taller purple stems, darker green foliage, light pink flowers, and rose colored calyxes compared to the seed parent.

2 Drawing Sheets

Latin name: *Agastache* hybrid.
Cultivar name: 'Velvet Crush'.

BACKGROUND OF THE INVENTION

The present invention relates to a new and distinct hybrid of *Agastache* plant named 'Velvet Crush' characterized by the combination of taller purple stems, darker green foliage; light pink flowers, and rose color calyxes on 80 cm plants compared to the seed parent. The new *Agastache* hybrid was raised as a seedling from open pollinated seed sown from the seed parent *Agastache cana* 'Bolero', not patented, in Hebron, Ill. in 2015. The selection of the new plant was due to its' taller purple stems, light pink flowers, and rose colored calyxes compared to the seed parent. Initial asexual reproduction has taken place at a nursery in Hebron, Ill. since 2016 by means of vegetative cuttings. The new *Agastache* hybrid has shown to be stable and identical in reproduction to the initially discovered plant after rooting over 300 plants from 2015 to 2016. No plants of the new *Monarda* have been sold in this country, or anywhere in the world, prior to the filing of this application, nor has any disclosure of the new plant been made prior to the filing of this application with the exception of that which was disclosed within one year of filing of this application and was either derived directly or indirectly for the inventor.

SUMMARY OF THE INVENTION

The new *Agastache* hybrid plant named 'Velvet Crush' characterized by taller purple stems, light pink flowers, and rose colored calyxes compared to the seed parent have been observed to be unique and stable. For purpose of comparison the new plant will be referred to as 'Velvet Crush'.

Plants of 'Velvet Crush' can be compared to the seed parent plant of *Agastache cana* 'Bolero', not patented. 1. The 'Velvet Crush' plant is taller growing to 80 cm while *Agastache cana* 'Bolero' grows to 40 cm. 2. The 'Velvet Crush' plant has a flower color of N78 C while *Agastache cana* 'Bolero' has a darker flower color of N88 A and also has a thicker flower head.

Plants of 'Velvet Crush' can also be compared to another pink flowered *Agastache pallida* 'Globetrotter', not patented. 1. The 'Velvet Crush' plant is short growing to 80 cm while *Agastache pallida* 'Globetrotter' grows to 100 cm. 2. The 'Velvet Crush' plant has a flower color of N78 C while *Agastache pallida* 'Globetrotter' has a flower color of lilac-pink with red rose calyxes.

DESCRIPTION OF PHOTOGRAPHS

Figure 1:
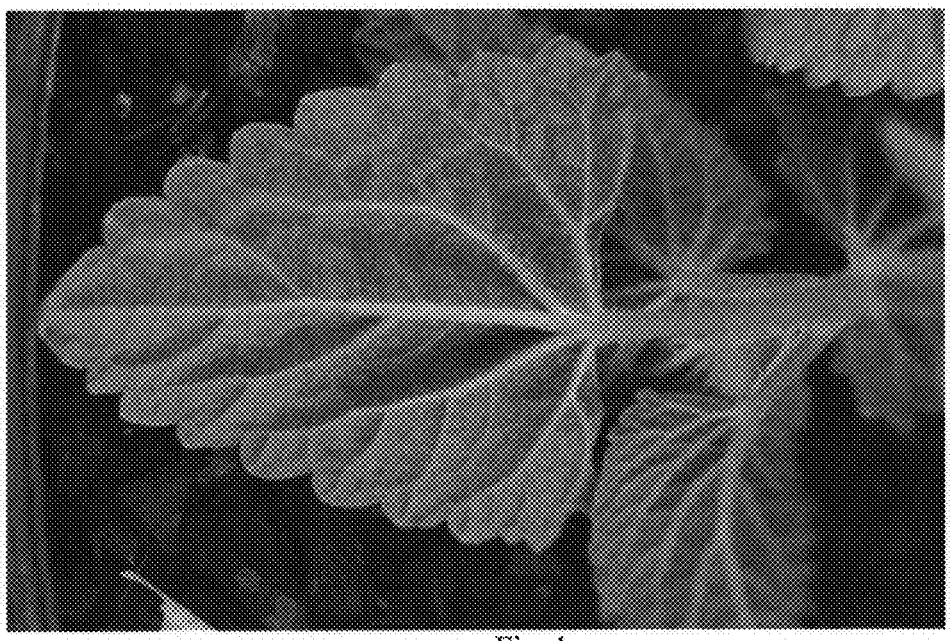
Figure 2:
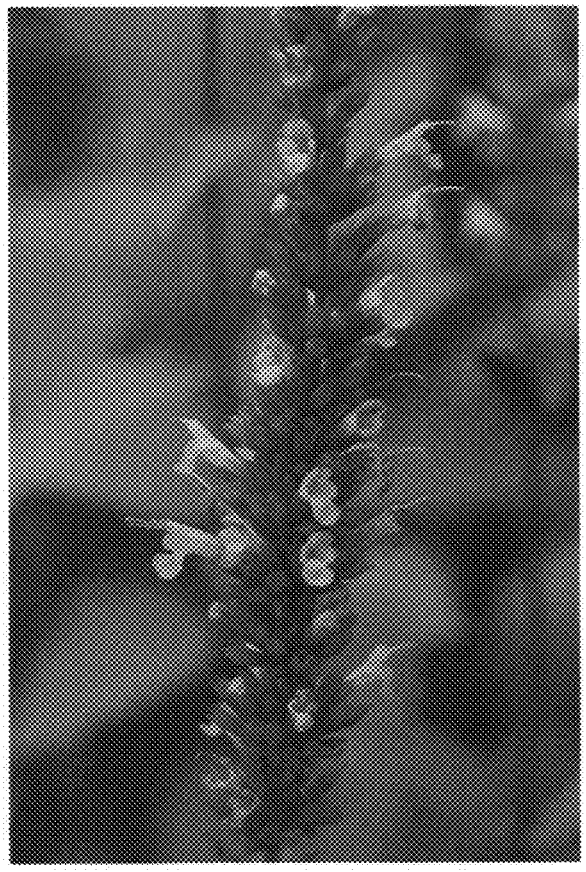
Figure 3:
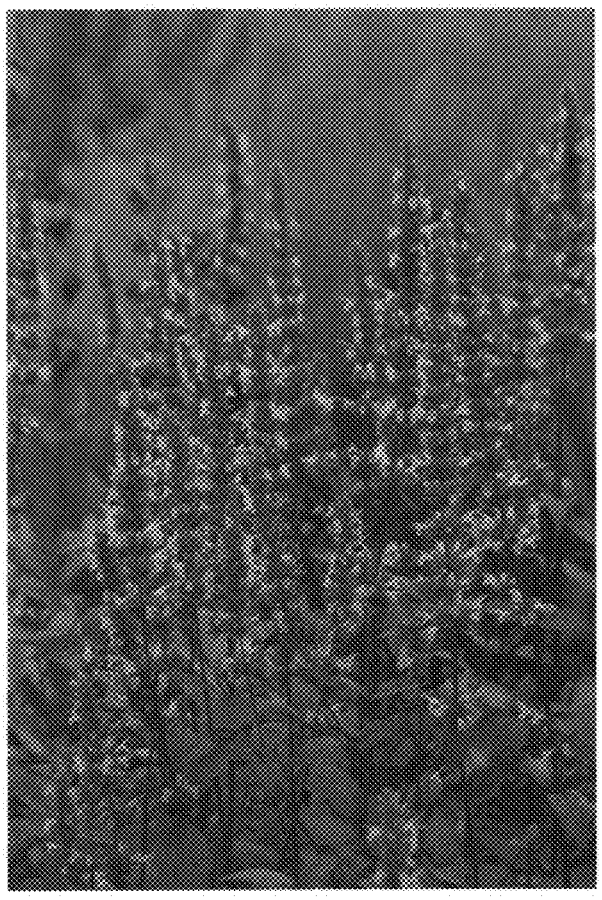

Plants pictured in the drawing were grown for one year.
FIG. 1. Close up of the backside of the foliage.
FIG. 2. Close up of the flower.
FIG. 3. A group of potted plants.

DETAILED BOTANICAL DESCRIPTION

In the following description, color references are made to The Royal Horticultural Society Colour Chart (2001). Plants used for the description were grown for one year. Measurements and numerical values represent averages of typical plants.

Plant description:
*Botanical classification.*—*Agastache* hybrid.
Form: Upright, mounded. Flower stems arise from the roots; Moderate branching, with numerous crowded flower spikes.
Parentage:
*Female, or seed, parent.*—*Agastache cana* 'Bolero'.
*Male, or pollen, parent.*—*Agastache* seedling, unnamed.
Propagation: Type: cutting, — By softwood cuttings.
Height: 80 cm from soil to top of flowers; Width: 60 cm.
Growth: Herbaceous perennial, broad upright, moderate vigor.
*Roots*.—Fine, compact, dense, freely branching, brown 199 C.

Stem:
*Form*.—Quadrangular, strong.
*Color*.—137 C at the base, purple at the exposed parts at times N77 A, being color 147 B on the exposed sides at times with both colors at times.
Texture: Smooth glabrous.
Branching: Moderate branching from the stem, typically 8 lateral branches, no pinching required.
*Diameter*.—9 mm.
*Length*.—80 cm.
*Internode length*.—Ranges from 2-15 cm.
*Quantity*.—Up to 14 flowering branches ranges from 2-15 cm.
Foliage:
*Arrangement*.—Opposite, simple.
*Number of leaves per branch*.—32, 16 pairs.
*Size of leaf*.—Length: 7 cm on average, shorter at tops of stems. Width: 4 cm.
*Shape of leaf*.—Lanceolate.
*Shape of tip*.—Acuminate.
*Shape of base*.—Rounded
*Texture*.—Smooth, glabrous.
*Margin type*.—Dentate.
*Color*.—Young and Mature leaves: Upper surface: 137 A. Lower surface: close to 147 B green also some purple 79 A on new growth.
*Fragrance*.—When rubbed, a typical anise scent.
*Petioles*.—Length: 15 mm on average for lower leaves; 1 cm or less on average for other leaves. Diameter: 1-1.5 mm. Color: 147 B.
*Veins*.—Pattern: Pinnate. Color: Upper surface: 137 A. Lower surface: hints of N77 A but mostly 147 B.
Durability: Highly durable to stresses.
Response time to flower: About 2 months when grown in the containers.
Flower description:
Natural flowering season: Continuous from July into October.
Inflorescence type and habit: Branched, terminal verticillaster, labiate, no fragrance, individual flowers last about one week on the plant, self-cleaning.
Rate of flower opening: About 10% of flowers open at once, all flowers open in about 12 weeks.
Number of flowers: About 170 per spike; about 1000 flowers per lateral branch.
Bud:
*Shape*.—Obovate.
*Length*.—9 mm.
*Diameter*.—2-3 mm.
*Color*.—N78 A.
Inflorescence size:
*Diameter*.—2 cm.
*Height*.—25 cm.
Peduncle:
*Length*.—12 cm.
*Diameter*.—2 mm.
*Color*.—N78 C with some green areas close to 147 B.
*Orientation*.—Upright with secondary peduncles at 30-45°.
*Texture*.—Smooth.
*Strength*.—Strong.
*Petal arrangement*.—Labiate, corolla with 3-lobed upper lip and one 2-lobed lower lip having one main upper lobe and two smaller lower lobes.
*Size*.—15 mm high; 5 mm wide.
*Margin*.—Entire.
*Tip shape*.—Emarginate upper lip; rounded lower lip.
*Length*.—Average upper lip: 15 mm; average lower lip: 13 mm.
*Width*.—Average upper lip: 5 mm; average lower lip: 3 mm.
*Petal quantity*.—5, fused at base.
*Petal apex shape*.—Upper lip; broad elliptic; folded; lower lip; spathulate.
*Texture*.—Upper and lower surfaces: smooth glabrous.
*Aspect*.—30-90° angle to stem tip.
*Petaloids*.—None.
Color:
*Petals*.—When opening: Upper surface: N78 C. Lower surface: N78 C. Fully opened: N78 C. Lower surface: N78 C.
Calyx:
*Arrangement*.—5 sepals fused into a tube at 75% of the length.
*Height*.—9 mm.
*Diameter*.—2-3 mm.
*Shape*.—Tubular.
*Sepals*.—Shape: Elliptic with acute tip and crenate base. Size: Average 9 mm long; 1mm or less wide. Margin: Entire. Texture. — Glabrous, smooth.
Color: Outer surface: N78 A. Inner surface: N78 A. Bracts: 2 bracts under each whorl of flowers; deltoid shape with apiculate tip; upper surface 147 B lower surface 139 C with a pink spot or streaks. Bract tissue; 7 mm long, 2 mm wide; Color at base N77 A and tip 79 A.
Reproductive organs:
Stamens:
*Number*.—4.
*Filament length*.—12 mm.
*Anthers*.—Shape: Basifixed, elliptic. Length: 1 mm. Color: White.
*Pollen*.—Color: White. Amount: Very low.
Pistil:
*Number*.—One.
*Length*.—12 mm.
*Style*.—Length: 12 mm. Color: N78 A.
*Stigma*.—Shape: Cleft (2 parted). Color: N78 A. Ovary color: N78 A.
Seeds and fruits: Brown and round 1 mm long and 1 mm wide, color 200 B.
Disease/pest resistance: No unusual susceptibility to diseases or pests has been noted to date.
Temperature tolerance: Tolerate to heat at least up to 30° C. and cool at least down to USDA Zone 5.

I claim:

1. A new, distinct *Agastache* hybrid plant as shown and described, characterized by the combination of taller purple stems, darker green foliage, light pink flowers, and rose colored calyxes compared to the seed parent.

* * * * *